United States Patent
Xu et al.

(10) Patent No.: US 9,068,067 B2
(45) Date of Patent: Jun. 30, 2015

(54) FLEXIBLE UNDERFILL COMPOSITIONS FOR ENHANCED RELIABILITY

(75) Inventors: Dingying Xu, Maricopa, AZ (US); Nisha Ananthakrishnan, Chandler, AZ (US); Hong Dong, Perry Hall, MD (US); Rahul N. Manepalli, Chandler, AZ (US); Nachiket Raravikar, Gilbert, AZ (US); Gregory S. Constable, Chandler, AZ (US)

(73) Assignee: INTEL CORPORATION, Santa Clara, CA (US)

( * ) Notice: Subject to any disclaimer, the term of this patent is extended or adjusted under 35 U.S.C. 154(b) by 1145 days.

(21) Appl. No.: 12/890,545

(22) Filed: Sep. 24, 2010

(65) Prior Publication Data

US 2012/0074597 A1    Mar. 29, 2012

(51) Int. Cl.
| | |
|---|---|
| *C04B 41/49* | (2006.01) |
| *C08L 83/00* | (2006.01) |
| *C08G 77/00* | (2006.01) |
| *C08L 63/00* | (2006.01) |
| *C08G 65/48* | (2006.01) |
| *C08L 23/08* | (2006.01) |
| *H01L 21/56* | (2006.01) |
| *H01L 23/29* | (2006.01) |
| *C08G 59/32* | (2006.01) |
| *C08G 59/38* | (2006.01) |
| *H01L 23/00* | (2006.01) |

(52) U.S. Cl.
CPC .......... *C08L 23/0884* (2013.01); *H01L 21/563* (2013.01); *H01L 23/293* (2013.01); *H01L 24/16* (2013.01); *H01L 24/73* (2013.01); *H01L 24/92* (2013.01); *H01L 2224/16227* (2013.01); *H01L 2224/73204* (2013.01); *H01L 2224/92125* (2013.01); *H01L 2924/15311* (2013.01); *H01L 2924/3512* (2013.01); *C08G 59/3254* (2013.01); *C08G 59/38* (2013.01); *H01L 2224/16225* (2013.01)

(58) Field of Classification Search
CPC .................................................... C08L 23/0884
USPC .......................................................... 525/523
See application file for complete search history.

(56) References Cited

U.S. PATENT DOCUMENTS

| | | | | |
|---|---|---|---|---|
| 5,863,970 | A * | 1/1999 | Ghoshal et al. | 523/434 |
| 6,274,650 | B1 * | 8/2001 | Cui | 523/457 |
| 6,548,175 | B2 * | 4/2003 | Sachdev et al. | 428/414 |
| 6,620,512 | B2 | 9/2003 | Jayaraman et al. | |

(Continued)

OTHER PUBLICATIONS

Dow, "D.E.R. 732", 2009.*

(Continued)

*Primary Examiner* — Peter F Godenschwager
*Assistant Examiner* — David Karst
(74) *Attorney, Agent, or Firm* — Konrad Raynes Davda & Victor LLP; Alan S. Raynes

(57) ABSTRACT

Underfill materials for fabricating electronic devices are described. One embodiment includes an underfill composition including an epoxy mixture, an amine hardener component, and a filler. The epoxy mixture may include a first epoxy comprising a bisphenol epoxy, a second epoxy comprising a multifunctional epoxy, and a third epoxy comprising an aliphatic epoxy, the aliphatic epoxy comprising a silicone epoxy. The first, second, and third epoxies each have a different chemical structure. Other embodiments are described and claimed.

10 Claims, 2 Drawing Sheets

(56) References Cited

U.S. PATENT DOCUMENTS

| | | |
|---|---|---|
| 7,041,736 B2 | 5/2006 | Jayaraman et al. |
| 7,151,014 B2 | 12/2006 | Manepalli et al. |
| 7,202,304 B2 | 4/2007 | Jayaraman et al. |
| 7,339,276 B2 | 3/2008 | Manepalli et al. |
| 7,345,000 B2 * | 3/2008 | Kevwitch et al. .............. 438/758 |
| 7,926,697 B2 | 4/2011 | Shekhawat et al. |
| 7,948,090 B2 | 5/2011 | Manepalli et al. |
| 8,093,105 B2 | 1/2012 | Manepalli et al. |
| 8,354,467 B2 | 1/2013 | Shekhawat et al. |
| 8,377,550 B2 | 2/2013 | Swaminathan et al. |
| 2006/0079609 A1 * | 4/2006 | Nishioka et al. ............... 523/400 |
| 2006/0103028 A1 * | 5/2006 | Hazeyama et al. ............ 257/778 |
| 2006/0147719 A1 * | 7/2006 | Rubinsztajn et al. .......... 428/413 |
| 2007/0254410 A1 * | 11/2007 | Shinoda et al. ................ 438/127 |
| 2008/0207848 A1 * | 8/2008 | Morita et al. .................. 525/475 |
| 2008/0285247 A1 * | 11/2008 | Ji et al. .......................... 361/783 |
| 2009/0004317 A1 | 1/2009 | Hu et al. |
| 2009/0166897 A1 * | 7/2009 | Katsurayama et al. ....... 257/793 |
| 2009/0170247 A1 | 7/2009 | Shekhawat et al. |

OTHER PUBLICATIONS

Dow, "D.E.R. 736", 2009.*

* cited by examiner

FLEXIBLE UNDERFILL COMPOSITIONS FOR ENHANCED RELIABILITY

RELATED ART

In certain conventional electronic assembly manufacturing procedures, a die and a package substrate are brought into electrical contact with one another using solder bumps. A reflow operation is carried out by heating to a temperature greater than the melting point of the solder, and a solder connection is made between the pads on the die and pads on the substrate. A gap remains between the die and the substrate. A material such as a polymer is then typically placed into the gap between the chip and substrate, as an underfill encapsulant. One example of a package substrate is known as a ball grid array (BGA). BGA packages have a plurality of solder bumps located on an opposite surface that the die is attached to. Another reflow operation is carried out by heating to a temperature greater than the melting point of the solder bumps on the BGA package, and a solder connection is made between the package substrate and the board.

FIG. 1 illustrates certain features of one conventional assembly manufacturing process. As illustrated in FIG. 1, a dispenser 16 such as a needle is positioned adjacent to a die 10 coupled to a package substrate 12 through solder bumps 14. An underfill material 18 is dispensed on the substrate 12 next to the die attach area. The underfill material 18 may comprise, for example, an epoxy mixture, one or more hardeners, a toughening agent, an adhesion promoter or coupling agent, and a filler. With the application of heat, the underfill material 18 may be made to flow between the die 10 and substrate 12, using capillary action. The underfill material 18 may then be cured by heating the assembly to a temperature of, for example, about 150° C. The cured underfill material 18 surrounds the solder bumps 14 and protects the bumps and connection between the die 10 and substrate 12, as well as assist in supporting the die 10 on the substrate 12. The underfill may also act to distribute stresses such as coefficient of thermal expansion (CTE) mismatch-induced stresses over the entire surface. Such CTE mismatch-induced stresses may be generated during the repeated heat cycles during the various processing operations. In addition, the underfill may act to inhibit moisture and other contamination from reaching the interconnection region between the die and substrate.

BRIEF DESCRIPTION OF THE DRAWINGS

Embodiments are described by way of example, with reference to the accompanying drawings, which are not drawn to scale, wherein.

DETAILED DESCRIPTION

Figure 1:
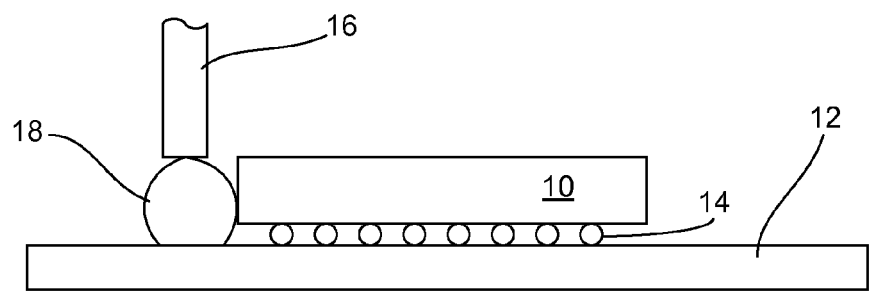
FIG. 1 illustrates a side cross-sectional view of a conventional processing operation in which an underfill material is dispensed on a package substrate.

Certain embodiments relate to underfill materials and their use in the formation of electronic assemblies.

Conventional underfill compositions have been found to suffer from electrical failures brought on by propagation of underfill sidewall delamination and underfill cracking in reliability tests. In addition, the volatility of certain aliphatic epoxies and hardener materials used in conventional underfill compositions lead to reactions that form outgassing of undesirable intermediates, which may contaminate the processing equipment or cause other environmental problems. For example, a reaction between an amine hardener and an aliphatic epoxy in the presence of heat, during a curing process, may result in the formation of an undesirable polymer intermediate, as set forth in the reaction process example below:

Reaction Process Example 1

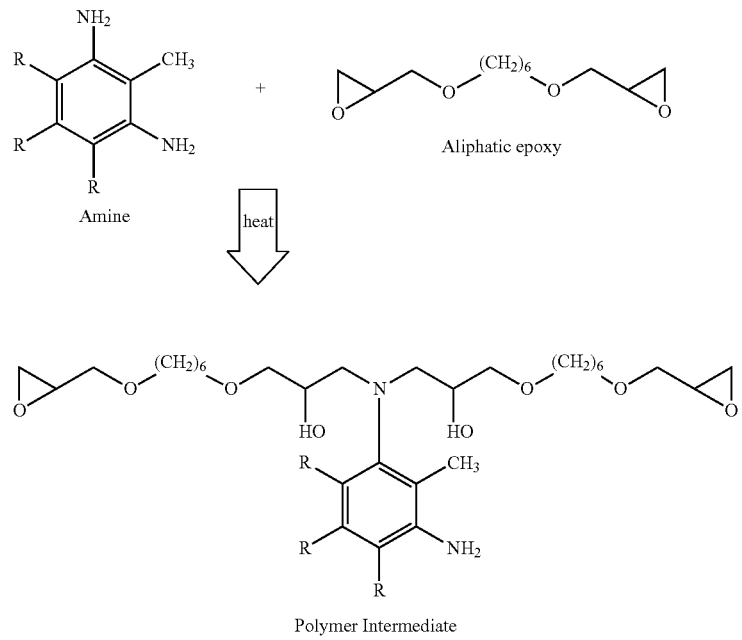

Such a polymer intermediate may stain processing equipment and walls.

Certain embodiments relate to underfill compositions that are formulated to inhibit the formation of intermediates that contaminate the environment, as well as reduce the occurrence of electrical failures of large die BGA packages caused by underfill fillet cracking, and improve reliability.

In certain embodiments, a conventional aliphatic epoxy such as that set forth in the reaction process example 1 is replaced with an aliphatic epoxy component having a different chemical structure. Such a different aliphatic epoxy may, in certain embodiments, be selected from silicone epoxy and glycol epoxy structures.

An underfill composition in accordance with one such group of embodiments includes the use of a silicone epoxy together with other epoxies. Such other epoxies may include a variety of suitable bisphenol epoxies and multifunctional epoxies. Multifunctional epoxies include two or more epoxide groups for the purposes of crosslinking. In one embodiment, the underfill includes a plurality of constituents, including first, second, and third epoxies, the epoxies having different chemical structures, the first epoxy a bisphenol F (bis-F) epoxy, the second epoxy a multifunctional epoxy, and the third epoxy a linear silicone epoxy. In certain embodiments, the silicone epoxy may have the following structure, wherein R is selected from the group consisting of methyl ($CH_3$) and ethyl ($C_2H_5$) groups:

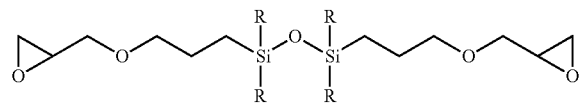

In one specific embodiment, each R is a methyl group ($CH_3$) and the structure has the chemical formula $C_{16}H_{34}O_5Si_2$. In other embodiments, there may be some R sites with a methyl group and some R sites with an ethyl group.

It is believed that the addition of the linear silicone epoxy into the epoxy matrix, in accordance with certain embodiments, results in an increased matrix ductility and toughness of the underfill.

Another embodiment including a silicone epoxy includes a linear epoxy containing a flexible substituted silicone structure, for example, the structure set forth below, where R is selected from the group consisting of methyl and ethyl groups:

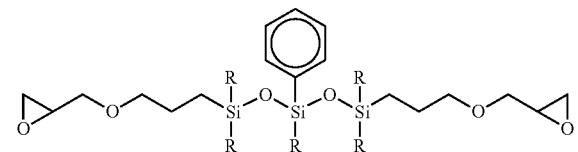

In one specific embodiment, each R is a methyl group ($CH_3$) and the structure has the chemical formula $C_{23}H_{43}O_6Si_3$. In other embodiments, there may be some R sites with a methyl group and some R sites with an ethyl group.

An underfill composition in accordance with another group of embodiments includes the use of a glycol epoxy together with other epoxies. Such other epoxies may include a variety of suitable bisphenol epoxies and multifunctional epoxies. In one embodiment, the underfill includes a plurality of constituents, including first, second, and third epoxies, the first epoxy a bis-F epoxy, the second epoxy a multifunctional epoxy, and the third epoxy selected from a linear polypropylene glycol epoxy or a linear polyethylene glycol epoxy. One embodiment includes a polypropylene glycol epoxy having the following structure:

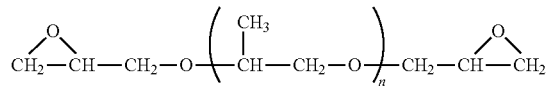

where n is in the range of 3 to 9. One specific embodiment includes n equal to 9. The polypropylene glycol epoxy with n equal to 9 is available from Dow Chemical Co., as D.E.R.™ 732 liquid epoxy resin.

Another embodiment includes a polyethylene glycol epoxy having the following structure:

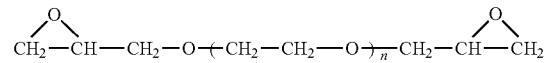

where n is in the range of 6 to 12.

It is believed that the addition of the linear polypropylene or polyethylene glycol epoxy into the epoxy matrix results in an increased matrix ductility and toughness of the underfill.

In addition to the epoxy components described above, underfill embodiments may also include one or more of certain other suitable components, including, but not limited to, hardening agents, tougheners, adhesion promoters, and fillers. An example of a hardening agent is the amine set forth in the reaction process example 1 set forth above. A filler (for example, $SiO_2$) may in certain embodiments be present in an amount of about 50-70 weight percent.

Figure 2:
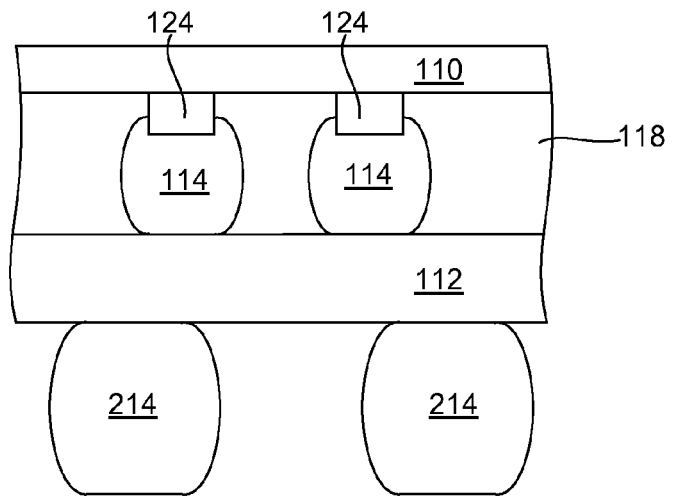
FIG. 2 illustrates a view of a portion of an assembly including a die coupled to a BGA substrate, with an underfill material positioned between the die and substrate, in accordance with certain embodiments.

FIG. 2 illustrates a cross-sectional view of an electronic assembly, in accordance with certain embodiments. As seen in FIG. 2, an underfill material 118 is placed into a region between a body such as a die 110 and a body such as a BGA substrate 112. The die 110 may include a plurality of bonding pads 124 thereon. The die 110 is electrically coupled to regions on the BGA substrate 112 through solder 114 that is in contact with the bonding pads 124. The BGA substrate 112 may include a plurality of solder bumps 214 for coupling to a board, as well as other features such as bonding pads (not shown). The underfill material 118 may include an epoxy mixture such as those described in certain embodiments above, including a bisphenol epoxy, a multi-functional epoxy, and an epoxy selected from the group consisting of a silicone epoxies and glycol epoxies. Other materials such as fillers and additives may also be present in the underfill material 118. Once the under material 118 is properly positioned, it may be cured.

Figure 3:
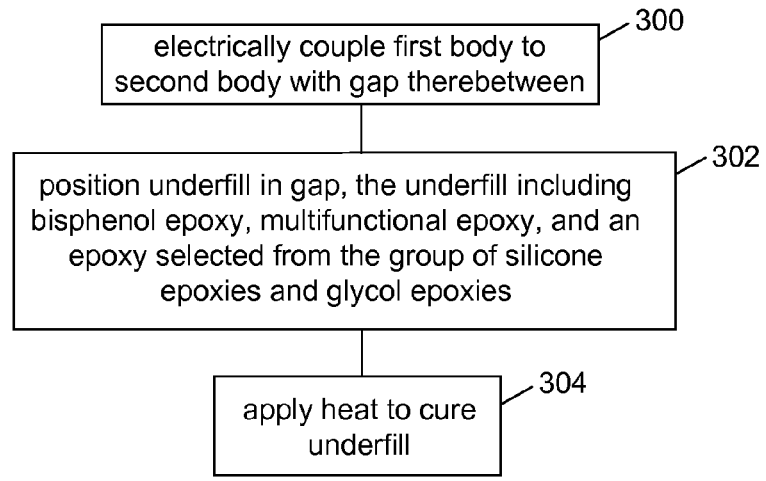
FIG. 3 illustrates a flow chart of operations in a process for forming an assembly using an underfill material, in accordance with certain embodiments.

FIG. 3 is a flow chart showing a number of operations in accordance with certain embodiments. Box 300 is electrically coupling a first body (for example, a die), to a second body (for example, a package substrate), using a method such as, for example, a C4 (controlled collapse chip connection) process, in which a gap remains between the first body and the second body. Solder bumps may be used to make the electrical connection between the first body and the second body. Box 302 is positioning an underfill material including an epoxy mixture, including a bisphenol epoxy, a multifunctional epoxy, and an epoxy selected from silicone epoxies and glycol epoxies, between the first body and the second body. Box 304 is applying heat to cure the underfill. Various additions and/or modifications may be made to the above operations where suitable.

Embodiments such as described above may have one or more of the following advantages, including: (1) providing enhanced resistance to cracking as compared with conventional underfill compositions; and (2) reducing volatile outgassing and contamination during processing due to the use of less volatile epoxy mixture.

Figure 4:
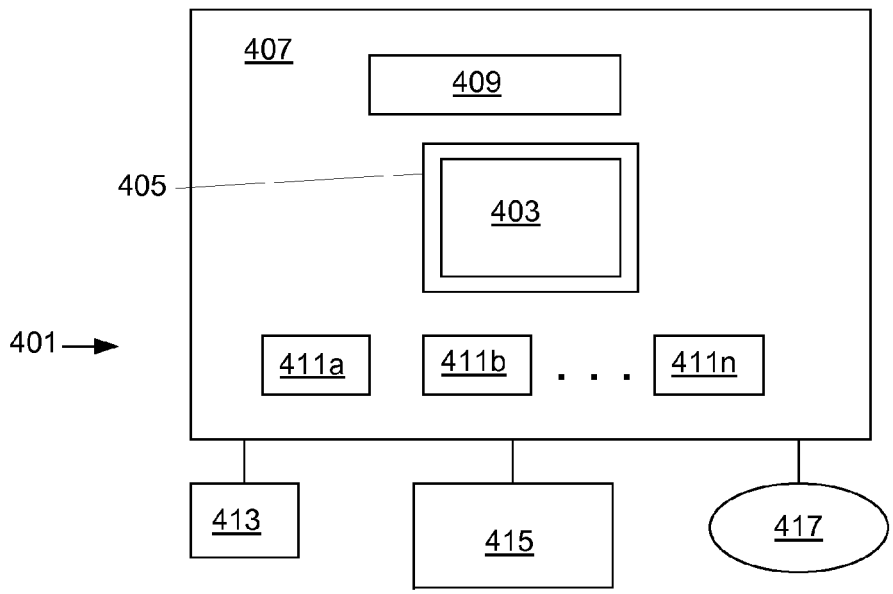
FIG. 4 illustrates an electronic system arrangement in which embodiments may find application.

Assemblies including, for example, a package substrate and die joined together as described in embodiments above may find application in a variety of electronic components, at various interconnection levels within the assembly. FIG. 4 schematically illustrates one example of an electronic system environment in which aspects of described embodiments may be embodied. Other embodiments need not include all of the features specified in FIG. 4, and may include alternative features not specified in FIG. 4.

The system 401 of FIG. 4 may include at least one central processing unit (CPU) 403. The CPU 403, also referred to as a microprocessor, may be a die which is attached to an integrated circuit package substrate 405, which is then coupled to a printed circuit board 407, which in this embodiment, may be a motherboard. The CPU 403 on the package substrate 405 is an example of an electronic device assembly that may be formed in accordance with embodiments such as described above, including an underfill material comprising the epoxy mixtures described above. A variety of other system components, including, but not limited to memory and other components discussed below, may also include die and substrate structures formed in accordance with the embodiments described above.

The system 401 may further include memory 409 and one or more controllers 411a, 411b . . . 411n, which are also disposed on the motherboard 407. The motherboard 407 may be a single layer or multi-layered board which has a plurality of conductive lines that provide communication between the circuits in the package 405 and other components mounted to the board 407. Alternatively, one or more of the CPU 403, memory 409 and controllers 411a, 411b . . . 411n may be disposed on other cards such as daughter cards or expansion cards. The CPU 403, memory 409 and controllers 411a, 411b . . . 411n may each be seated in individual sockets or may be connected directly to a printed circuit board. A display 415 may also be included.

Any suitable operating system and various applications execute on the CPU 403 and reside in the memory 409. The content residing in memory 409 may be cached in accordance with known caching techniques. Programs and data in memory 409 may be swapped into storage 413 as part of memory management operations. The system 401 may comprise any suitable computing device, including, but not limited to, a mainframe, server, personal computer, workstation, laptop, handheld computer, handheld gaming device, handheld entertainment device (for example, MP3 (moving picture experts group layer-3 audio) player), PDA (personal digital assistant) telephony device (wireless or wired), network appliance, virtualization device, storage controller, network controller, router, etc.

The controllers 411a, 411b . . . 411n may include one or more of a system controller, peripheral controller, memory controller, hub controller, I/O (input/output) bus controller, video controller, network controller, storage controller, communications controller, etc. For example, a storage controller can control the reading of data from and the writing of data to the storage 413 in accordance with a storage protocol layer. The storage protocol of the layer may be any of a number of known storage protocols. Data being written to or read from the storage 413 may be cached in accordance with known caching techniques. A network controller can include one or more protocol layers to send and receive network packets to and from remote devices over a network 417. The network 417 may comprise a Local Area Network (LAN), the Internet, a Wide Area Network (WAN), Storage Area Network (SAN), etc. Embodiments may be configured to transmit and receive data over a wireless network or connection. In certain embodiments, the network controller and various protocol layers may employ the Ethernet protocol over unshielded twisted pair cable, token ring protocol, Fibre Channel protocol, etc., or any other suitable network communication protocol.

The terms "a" and "an" as used herein denote the presence of at least one of the referenced item, and do not denote a limitation of quantity. In addition, terms such as "first", "second", and the like as used herein to not necessarily denote any particular order, quantity, or importance, but are used to distinguish one element from another.

While certain exemplary embodiments have been described above and shown in the accompanying drawings, it is to be understood that such embodiments are merely illustrative and not restrictive, and that embodiments are not restricted to the specific constructions and arrangements shown and described since modifications may occur to those having ordinary skill in the art.

What is claimed:

1. An underfill composition comprising:
an epoxy mixture comprising a first epoxy comprising a bisphenol epoxy, a second epoxy comprising a multifunctional epoxy, and a third epoxy comprising an aliphatic epoxy, the aliphatic epoxy comprising a silicone epoxy; the first, second, and third epoxies each having a different chemical structure; and
a filler;
wherein the silicone epoxy has the following structure:

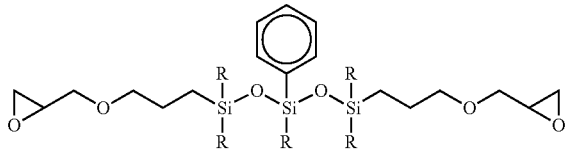

where R is a group selected from the group consisting of methyl groups and ethyl groups, and wherein at least one of the R sites includes a methyl group and at least one of the R sites includes an ethyl group.

2. The underfill composition of claim 1, wherein the bisphenol epoxy comprises a bisphenol F epoxy.

3. The underfill composition of claim 1, further comprising a hardener component.

4. The underfill composition of claim 1, wherein the filler comprises an oxide.

5. The underfill composition of claim 1, wherein the filler comprises $SiO_2$ present in an amount in the range of 50 to 70 weight percent of the composition.

6. An underfill composition comprising:
an epoxy mixture comprising a first epoxy comprising a bisphenol epoxy, a second epoxy comprising a multifunctional epoxy, and a third epoxy comprising an aliphatic epoxy, the aliphatic epoxy comprising a silicone epoxy; the first, second, and third epoxies each having a different chemical structure; and
a filler;
wherein the silicone epoxy has the following structure:

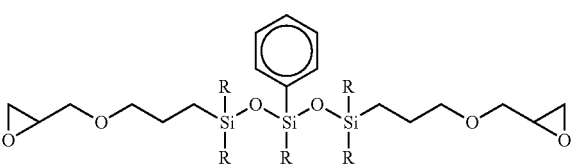

where R is a group selected from the group consisting of methyl groups and ethyl groups, wherein a plurality of the R sites include a methyl group and a plurality of the R sites include an ethyl group.

7. The underfill composition of claim 6, wherein the bisphenol epoxy comprises a bisphenol F epoxy.

8. The underfill composition of claim 6, further comprising a hardener component.

9. The underfill composition of claim 6, wherein the filler comprises an oxide.

10. The underfill composition of claim 6, wherein the filler comprises Sift present in an amount in the range of 50 to 70 weight percent of the composition.

* * * * *